| United States Patent [19] | [11] | 4,294,818 |
|---|---|---|
| McMichael et al. | [45] | Oct. 13, 1981 |

[54] METHODS AND MATERIALS FOR DETECTION OF MULTIPLE SCLEROSIS

[75] Inventors: John McMichael, Cambridge Springs, Pa.; Ellis L. Kline, Pendleton, S.C.; James G. Spaulding, Saegertown, Pa.

[73] Assignee: University Patents, Inc., Norwalk, Conn.

[21] Appl. No.: 61,759

[22] Filed: Jul. 30, 1979

[51] Int. Cl.³ .................... G01N 33/48; G01N 33/50; G01N 33/54
[52] U.S. Cl. .................................. 424/12; 23/230 B; 260/112 R; 260/112 B; 424/1.5; 424/8; 424/85; 424/88; 424/177
[58] Field of Search ............... 424/3, 8, 12, 85, 86, 424/88, 90, 177; 23/230 B; 260/112 R, 112 B

[56] References Cited

U.S. PATENT DOCUMENTS

| 3,864,481 | 2/1975 | Hashim | 424/177 |
| 4,113,858 | 9/1978 | Hashim | 424/177 |

OTHER PUBLICATIONS

Kabat, Structural Concepts in Immunology & Immunochem., Reinhart–Winston, NY, 2nd Ed. 1976, pp. 352, 403–409, 471–486.
Barrett, Textbook of Immunol. C.V. Mosby Co., St. Louis, 2nd Ed. 1974 pp. 323–329.
Arnason, Chem. Abs., vol. 89, 1978 Ab No. 89:21565n.
Smith, Chem. Abs., vol. 90, 1979 Ab No. 90:149780v.
Angers, Chem. & Eng. News, Apr. 9, 1979 p. 22.
Frick, Chem. Abs., vol. 88, 1978 Ab No. 88:48671p.
Gosseye-Lissoir, Chem. Abs. vol. 88, 1978 Ab. No. 88:48674s.
Bakouche, Chem. Abs. vol. 72, 1970 Ab. No. 119353u.

*Primary Examiner*—Anna P. Fagelson
*Attorney, Agent, or Firm*—Merriam, Marshall & Bicknell

[57] ABSTRACT

Methods and materials for diagnosis of a multiple sclerosis disease state. Antigenic blood fractions from patients clinically diagnosed for multiple sclerosis are employed to generate heterologous species antibodies. Novel antibody preparations are employed to detect the presence or absence, in a blood sample of a patient to be tested, of immunologically significant components specifically associated with a multiple sclerosis disease state.

6 Claims, No Drawings

METHODS AND MATERIALS FOR DETECTION OF MULTIPLE SCLEROSIS

BACKGROUND

The present invention relates generally to diagnosis of a multiple sclerosis disease state in humans and more specifically to novel antigen and antibody preparations and immunological reagents containing same which are useful in diagnosis of multiple sclerosis.

Multiple sclerosis, sometimes referred to as disseminated sclerosis, is a slowly progressive disease of the central nervous system characterized morphologically by disseminated patches of demyelinization in the brain and spinal cord and clinically by multiple symptoms and signs with remissions and exacerbations.

The etiology of multiple sclerosis is essentially unknown and the disease has been variously attributed to: autoimmune mechanisms; infection by a slow virus; toxic agents such as metallic poisons; metabolic elements such as myelin-splitting factor; and vascular lesions resulting from abnormal blood clotting mechanisms.

Among the varied symptoms of the multiple sclerosis disease state are sensory (especially visual) disorders, spastic weakness of limbs, cerebellar ataxia, nystagmus, bladder dysfunction, mood disorders and combinations of two or more such symptoms.

Diagnosis of the disease state is virtually impossible owing to the overlap of the above-noted symptoms of multiple sclerosis and similar symptoms of other disease states. Diagnosis of the disease state is most frequently premised upon a "classic" history of remissions and exacerbations of the various symptoms over a period of years, combined with systematic elimination of other possible disease involvements which give rise to similar symptoms. Collateral testing at substantial cost and often physical discomfort to the patient is performed in order to "eliminate" e.g., intracranial lesions, cerebrovascular accidents, acoustic neuroma, cerebellar tumors, gliomas of the brain stem, spinal cord tumors, amyotrophic lateral sclerosis, syphilis, pernicious anemia, arthritis of the cervical spine, ruptured intervertebral disk, platybasia, and hereditary ataxia as the source of symptoms.

Substantial efforts have been directed toward development of diagnostic methods and materials useful in the early diagnosis of multiple sclerosis. Positive results in colloidal gold tests on cerebrospinal fluids are considered supportive, but not dispositive of, positive diagnosis. The same is true of testing for elevated gamma globulin in cerebrospinal fluids—the test tends to verify diagnosis in advanced cases but is not helpful in early diagnosis. Similarly, active demyelinization associated with the disease frequently is signified by elevation of analytical results in basic protein assay testing of spinal fluid, but test levels drop rapidly once acute exacerbation is over. Non-dispositive correlations have been made between presence of the disease state and elevated levels of measles antibodies in serum and cerebrospinal fluids. Finally, certain researchers have proposed that electron microscopic examination of lymphocytes for certain distinct morphological changes may provide a fruitful basis for diagnosis of multiple sclerosis.

The character of the most recent advances in the art is exemplified by the disclosures of Angers, et al., reported in Chemical & Engineering News, page 22, Apr. 9, 1979. Briefly summarized, Angers, et al. assert the usefulness of a leukocyte adherence inhibition (LAI) test using an essentially non-specific blood extract (so-called "Multiple Sclerosis Related Material") from the blood of multiple sclerosis patients in relapsing or progressive disease states. The LAI test involves measurement of decreasing ability of test sample erythrocytes to adhere to a glass surface after incubation in MSRM. The rather complicated, time consuming and expensive procedure is alleged to be approximately ninety percent accurate in identifying multiple sclerosis patients and 95 percent accurate in identifying non-multiple sclerosis patients.

There therefore exists a most substantial need in the art for diagnostic methods and materials for rapidly, simply and accurately determining the presence of a multiple sclerosis disease state, Desirably, such methods should be highly specific for multiple sclerosis (i.e., should not generate false positive results in the instance of other central nervous system diseases). Further, such methods should be capable of ascertaining the presence of the disease state in its early stages, should be operatively independent of disease exacerbation and remission, should not involve painful or hazardous withdrawals of patient tissue samples, and should preferably involve standardized laboratory techniques which do not require expensive or difficult-to-operate apparatus.

BRIEF SUMMARY

According to a principal aspect of the present invention, antibody preparations are provided which are specifically immunologically reactive with antigenic substances associated with lymphocytes of patients having multiple sclerosis. The antibody preparations are employed to develop diagnostic reagents suitable for use in standardized immunological assays applied to lymphocytes obtained from patients suspected of having the disease.

Other aspects and advantages of the present invention will be apparent to those skilled in the art upon consideration of the following detailed description thereof.

DETAILED DESCRIPTION

The operative basis of the present invention resides at least in part in the discovery of an antigenic substance uniquely associated with the blood (and predominantly the lymphocytes) of human patients clinically diagnosed as suffering from multiple sclerosis. This antigen was further discovered to be capable of prompting quantitative formation of specific antibodies in immunologically active, heterologous species animals (e.g., rabbits). Preparations containing the specific antibodies so generated were found to be immunologically reactive with lymphocytes of multiple sclerosis patients essentially independently of the stage of disease development or the remitted or exacerbated state of the patient at the time of lymphocyte sampling. Significantly, the antibody preparations are essentially non-reactive immunologically with non-multiple sclerosis patients, even those with central nervous system disorders frequently mis-diagnosed relative to multiple sclerosis.

Antibody preparations of the present invention may be suitably employed in a variety of immulogical procedures including immunodiffusion assays, fluorescent antibody assays, radioimmunoassays and the like, each of which would involve development of reagents appropriate for such use.

The following examples illustrate practice of the invention according to certain presently preferred procedures. More specifically, they treat: preparation of lymphocytes for use either as an antigenic inoculant or as a patient test sample; development of specific antibody preparations; and use of antibody preparations in an immunodiffusion assay.

EXAMPLE 1

Lymphocytes employed as antigenic inoculants to develop antibody preparations and lymphocytes employed in diagnostic testing according to the present invention may identically be prepared by the following exemplary procedure. A 10 ml sample of venous blood is collected in an evacuated tube and thoroughly mixed with, e.g., 0.5 ml of 0.1 M sodium citrate. Lymphocytes are separated from the blood using Lymphocyte Preparation Medium (Bionetics) and, following low speed centrifugation, the lymphocyte layer is removed. Cells are subjected to homogenization to disrupt cell membranes and the homogenized lymphocytes may be stored (at $-80°$ C.) until needed. The antigenic component of such lymphocytic preparations appears to be highly stable, remaining immunologically "intact" at refrigerated temperatures for at least eight months and capable of withstanding at least four "freeze-thaw" cycles ($-80°$ to $22°$ C.).

EXAMPLE 2

Antibody preparations of the invention may be obtained according to the following illustrative procedure. Six ml of homogenized lymphocytes, prepared according to Example 1 and obtained from one or more patients positively clinically diagnosed for multiple sclerosis, is added to 4 ml of Freund's Complete Adjuvant and mixed to form a stable suspension. Rabbits are each given four 0.5 ml. intramuscular injections of the lymphocyte/adjuvant suspension (two on each side) and 1 ml of homogenized lymphocytes without added adjuvant is administered to the marginal ear vein. Intramuscular injections are repeated at 7, 14 and 21 days after the initial inoculation. Two weeks after the last of the injections the animals are sacrificed and the blood is removed by cardiac puncture.

Serum is separated from whole blood and subjected to purification to remove non-specific antibodies and especially those raised in the animal in response to human lymphocytic constituents other than the multiple sclerosis antigenic component. Such separation is accomplished, for example, by serial absorptive contacts with lymphocyte homogenizate preparations from non-diseased control patients. Four serial contacts of one hour duration are adequate to "purify" the serum with, e.g., a 4 ml serum sample being treated with 1 ml aliquots of control lymphocyte homogenizate at $37°$ C. Antibody preparations so obtained are quite stable. Preliminary electrophoretic analysis indicates that specific multiple sclerosis antibody is likely to be a microglobulin.

EXAMPLE 3

Diagnostic testing of patient lymphocyte samples may be effected according to the following exemplary procedure. Employed are commercial immunodiffusion templates (Clinical Sciences, Inc.) having a central well and six additional wells radially outwardly spaced at a uniform distance from the central well. The gel medium is noble agar in 0.1 N barbitol buffer. A well volume of about 0.12 ml is appropriate. About 0.15 ml of antibody preparation (serum) according to Example 2 is placed in the central well. To three of the peripheral wells is added about 0.12 ml of lymphocyte homogenizate obtained according to Example 1 from a clinically diagnosed multiple sclerosis patient. To each of the remaining three cells is added about 0.12 ml of lymphocyte homogenizate obtained from the test patient. Templates are allowed to incubate at room temperature for 12 to 18 hours and then immersed in 0.85% saline for 4 hours at room temperature. Templates are then visually read for presence or absence of precipitin bands between the central and peripheral wells. Bands appearing between the central well and test sample wells and duplicating those between the central well and multiple sclerosis controls are indicative of a multiple sclerosis disease state in the patient. Absence of bands is read as being indicative of absence of the disease state.

EXAMPLE 4

Operability of the exemplary procedures of Example 3 is evidenced by the following results of two series of tests.

Table 1 below relates the results of 50 diagnostic tests performed on lymphocyte homogenizates obtained from residents of the Erie, Pennsylvania area. As indicated, lymphocytes were obtained from non-multiple sclerosis ("normal") patients, from clinically diagnosed multiple sclerosis patients ("MS"), and from patients clinically diagnosed for a central nervous system disease state other than multiple sclerosis (stroke). Immunodiffusion test data are designated "Pos" for a positive multiple sclerosis result and "Neg" for absence of the indicative precipitin bands. Test/clinical diagnosis correlation is signified by a "+", and a "−" signifies absence of such correlation.

TABLE I

| Sample Number | Test Result | Clinical Diagnosis | Test/Clinical Diagnosis Correlation |
|---|---|---|---|
| 1 | Pos | MS | + |
| 2 | Neg | Normal | + |
| 3 | Pos | MS | + |
| 4 | Pos | MS | + |
| 5 | Neg | Normal | + |
| 6 | Neg | Normal | + |
| 7 | Pos | MS | + |
| 8 | Neg | Stroke | + |
| 9 | Pos | MS | + |
| 10 | Neg | MS | − |
| 11 | Neg | Normal | + |
| 12 | Pos | MS | + |
| 13 | Neg | Normal | + |
| 14 | Pos | Stroke | − (a) |
| 15 | Neg | MS | − |
| 16 | Pos | MS | + |
| 17 | Pos | MS | + |
| 18 | Pos | MS | + |
| 19 | Pos | MS | + |
| 20 | Neg | Stroke | + |
| 21 | Neg | Normal | + |
| 22 | Pos | MS | + |
| 23 | Pos | Normal | − |
| 24 | Neg | Normal | + |
| 25 | Neg | Normal | + |
| 26 | Neg | Normal | + |
| 27 | Neg | Stroke | + |
| 28 | Neg | Normal | + |
| 29 | Pos | MS | + |
| 30 | Pos | MS | + |
| 31 | Pos | MS | + |
| 32 | Neg | Normal | + |
| 33 | Pos | MS | + |
| 34 | Pos | MS | + |
| 35 | Neg | MS | − |

TABLE I-continued

| Sample Number | Test Result | Clinical Diagnosis | Test/Clinical Diagnosis Correlation |
|---|---|---|---|
| 36 | Pos | MS | + |
| 37 | Pos | MS | + |
| 38 | Neg | MS | − |
| 39 | Pos | MS | + |
| 40 | Neg | Normal | + |
| 41 | Neg | MS | − |
| 42 | Neg | Normal | + |
| 43 | Pos | MS | + |
| 44 | Pos | MS | + |
| 45 | Pos | MS | + |
| 46 | Pos | MS | + |
| 47 | Pos | Stroke | − |
| 48 | Neg | Normal | + |
| 49 | Neg | Normal | + |
| 50 | Neg | Normal | + |

(a) Clinical diagnosis later changed to MS.

Table 2 below relates to the results of 33 diagnostic tests performed on lymphocyte homogenizates obtained from residents of the Kalamazoo, Michigan area. Once again, samples were obtained from normal, multiple sclerosis and other CNS disease patients as indicated.

TABLE 2

| Sample Number | Test Result | Clinical Diagnosis | Test/Clinical Diagnosis Correlation |
|---|---|---|---|
| 1 | Neg | Normal | + |
| 2 | Neg | Normal | + |
| 3 | Neg | MS | − |
| 4 | Neg | Bell's Palsy | + |
| 5 | Neg | Diabetes | + |
| 6 | Neg | SLE (a) | + |
| 7 | Neg | Stroke | + |
| 8 | Neg | Normal | + |
| 9 | Neg | Normal | + (b) |
| 10 | Neg | Normal | + (c) |
| 11 | Neg | Epilepsy, Sickle Cell | + |
| 12 | Neg | Normal | + |
| 13 | Pos | Normal | − (b) |
| 14 | Pos | SLE | − |
| 15 | Neg | MS | − |
| 16 | Neg | Normal | + |
| 17 | Neg | MS | − |
| 18 | Neg | Stroke | + |
| 19 | Pos | SLE | − |
| 20 | Neg | Stroke | + |
| 21 | Neg | Normal | + |
| 22 | Neg | MS | − |
| 23 | Neg | SLE | + |
| 24 | Neg | Epilepsy | + |
| 25 | Neg | SLE | + |
| 26 | Neg | Normal | + |
| 27 | Neg | Parkinson's | + |
| 28 | Neg | Stroke | + |
| 29 | Neg | Parkinson's | + |
| 30 | Neg | Normal | + |
| 31 | Neg | Normal | + |
| 32 | Neg | Normal | + |
| 33 | Pos | MS | + |

(a) Systemic Lupus Erythematosus
(b) Son of MS patient
(c) Wife of MS patient

Consistent with the foregoing disclosure, numerous modifications and variations in practice of the invention are expected to occur to those skilled in that art. As previously noted, antibody preparations of the invention are expected to be useful in providing a variety of immunological diagnostic reagents. In addition to usefulness in immunodiffusion assays, serum containing antibodies may be employed to sensitize immunologically inert particles (stabilized erythrocytes, latex beads and the like) which may be employed in agglutination tests. Isolation and purification techniques well known in the art may be applied to the antibody prepartions to secure the active component in more concentrated state which, in turn, may be employed in a "labeled" form as a reagent in fluorescent antibody and radioimmunoassay diagnositc techniques. Concentration of specific antibodies from serum antibody preparations is also expected to make possible the isolation and characterization of the specific lymphocyte antigen associated with the multiple sclerosis disease state together with antigenic components which currently appear to be present in substantially lesser concentrations in serum of multiple sclerosis patients. The antigen, in purified form, may be usefully employed not only in facilitating large scale quantitative antibody preparation but also as a diagnostic reagent component, especially in immunoassays of a "competitive" type. Such a purified antigen is likely to be useful as a therapeutic agent in the treatment of multiple sclerosis according to therapeutic techniques commonly known as provocative therapy. According to such techniques, low dosages of a disease-causitive antigenic substance are administered for the purpose of provoking a palliative systemic response in the patient.

What is claimed is:

1. A diagnostic reagent for use in serological determination of the presence of a multiple sclerosis disease state in a human patient, said reagent comprising heterologous species antibodies obtained by means of a heterologous species immune response to exposure to components of a homogenizate of lymphocytes of a human patient suffering from multiple sclerosis.

2. A reagent according to claim 1 wherein said antibodies are provided as a component of heterologous species serum.

3. A reagent according to claim 2 wherein the heterologous species serum is rabbit serum.

4. A diagnostic method for determining the presence of a multiple sclerosis disease state in a human patient, said method comprising the steps of:
   (a) forming a mixture of a homogenizate of lymphocytes of said patient with a diagnostic reagent according to claim 1; and
   (b) monitoring said mixture for an immunological reaction.

5. A method for preparation of antibodies specifically immunologically reactive with components of a homogenizate of lymphocytes of a patient suffering from a multiple sclerosis disease state, said method comprising:
   (a) administering to an immunolgoically active host animal of heterologous species animal a preparation of homogenized lymphocytes of a human patient having multiple sclerosis; and
   (b) isolating antibodies from the blood of said host animal.

6. A method according to claim 5 wherein said isolation step includes contacting serum obtained from said host animal with homogenized lymphocytes of a human not having multiple sclerosis, whereby antibodies not specific for multiple sclerosis lymphocytic components are removed from said serum.

* * * * *